US00PP10423P

United States Patent [19]

Stanley

[11] Patent Number: Plant 10,423

[45] Date of Patent: Jun. 2, 1998

[54] **DOGWOOD (*CORNUS FLORIDA*) NAMED 'AM-ERIKA TOUCH-O-PINK'**

[76] Inventor: Howard W. Stanley, HCO1, Box 278, Reidsville, Ga. 30453

[21] Appl. No.: 653,001

[22] Filed: May 24, 1996

[51] Int. Cl.[6] ..... A01H 5/00

[52] U.S. Cl. ..... Plt./53.2

[58] Field of Search ..... Plt./53.2

[56] References Cited

U.S. PATENT DOCUMENTS

P.P. 8,500 12/1993 Smith ..... Plt./53.2

*Primary Examiner*—James R. Feyrer
*Assistant Examiner*—Kent L. Bell
*Attorney, Agent, or Firm*—Needle & Rosenberg PC

[57] ABSTRACT

A new and distinct variety of dogwood, *Cornus florida*, is provided which forms extremely large and distinctive blooms wherein the petals are pink on the outside fading to almost white in the center. The plant produces larger than normal leaves and exhibits superior growth rate and a hardy resistance to disease.

2 Drawing Sheets

SUMMARY OF THE INVENTION

The new and improved variety of Dogwood, *Cornus florida*, named 'Am-erika Touch-O-Pink' was discovered through examination of over two million white Dogwood seedlings. The seed from which these seedlings were propagated was collected from native Dogwood trees in the costal plains section of Georgia. The improved Dogwood has several outstanding characteristics including, larger than normal leaves, extremely large and distinctive blooms, a superior growth rate and a hardy resistance to disease. The bracts are blushed pink at the margins; the pink color suffusing gradually to white, which predominates the bract lamina.

The new and improved dogwood variety 'Am-erika Touch-O-Pink' was first reproduced asexually in February, 1989 in Tatnall County, Ga. by grafting scions from the original parent plant. Other routes of asexual propagation are possible and include budding and cuttage. The improved characteristics of this Dogwood have been found to be stable and are strictly transmissible by such asexual propagation from one generation to another.

The new improved Dogwood variety meets the needs of the horticultural industry and is particularly well suited for use as attractive ornamentation in the landscape.

The new dogwood variety 'Am-erika Touch-O-Pink' presents a unique cultivar of dogwood, producing the large blooms previously only associated with pure white bracts, which also show the pink color found in other varieties. The enormous and unusually colored bracts are larger than any previously reported, and they are more than twice the size of the bracts typical of the pink-colored varieties. In full bloom, this tree presents a conspicuous splash of color which is unparalleled by existing trees and offers flowering stems of novel coloration which can be included in cut floral arrangements.

'Am-erika Touch-O-Pink' has extended the effective range of pink-colored dogwood varieties to the coastal plains of Georgia. Existing pink-colored cultivars do not bloom consistently in the coastal plains region, perhaps only blooming 1 out of every 4–5 years. The variety 'Am-erika Touch-O-Pink' has been observed in Tatnall County, Ga. for the past six years, and it has bloomed profusely each of those years.

BRIEF DESCRIPTION OF THE DRAWINGS

The accompanying drawing and photograph show typical specimens of the inflorescence and an entire, fully leafed-out tree, respectively. The drawing was adapted from 3 and 4 year old specimens of this variety as the bracts appear during March and April when grown outdoors in Reidsville, Ga.

DETAILED DESCRIPTION

Figure 1:
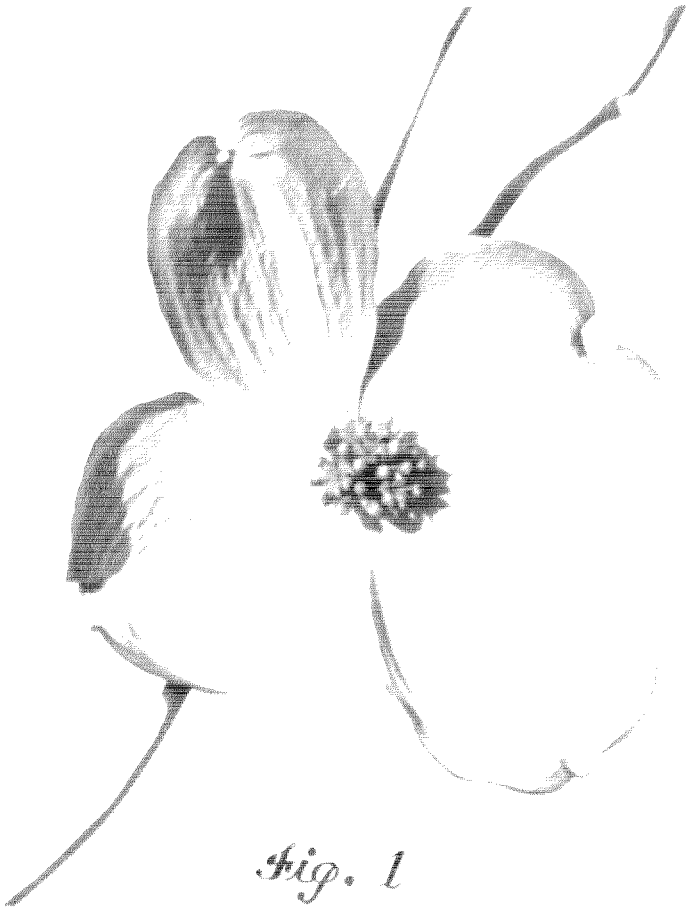
FIG. 1 shows a rendering of a specimen from 'Am-erika Touch-O-Pink' to illustrate a fully open inflorescence on bloom stage wood to show the shape, texture, and coloration of inner and outer bract pairs and the details and color of the reproductive organs. Also shown is early leaf formation from breaking vegetative buds.
Figure 2:
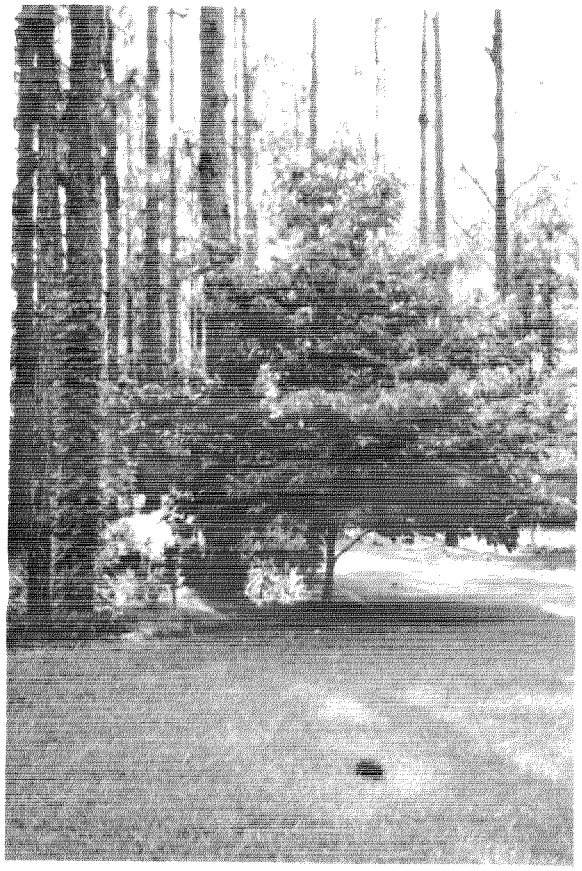
FIG. 2 is a photograph of a typical specimen of an entire 'Am-erika Touch-O-Pink' tree six years after its propagation from a scion of the original, parent plant, illustrating its summer foliage in Reidsville, Ga.

The description is based on the observation of two and three year old plants while in bloom and later in the growing season when leaves have reached full maturity.

Class: *Cornus florida*.

Plant:

*Height*.—Approximately 18–20 feet at full maturity; growing at approximately 3 feet per year reaching 12–15 feet in four years.

*Habit*.—Erect.

*Shape*.—Well-rounded, very conical shaped from the ground up. Very little pruning necessary. A typical specimen is slightly taller than it is wide; a 10 year old specimen that is approximately 22.5 feet tall is approximately 15 feet in diameter, measured at the bottom branches.

*Bark*.—In spring, the new growth bark is a light-tan to grey-tan color. As it matures through the season, the bark hardens and becomes completely grey. Exfoliating bark has not been noted on trees through 6 years of age.

Branches:

*Trunk*.—Diameter of 3½ to 4 inches within 4 years.

*Vegetative branches*.—Sub-branches more frequently seem to be stouter and spread more than the native dogwood. The branching angle is approximately 30 degrees from the horizontal, and the length of the branches shortens closer to the crown, creating the typical conical shape of the species in the cultivated landscape.

*Floral branches.*—The terminal branches produce 3–4 growth stems during the growing season, and each of these growth stems will produce 2–4 blooms per stem the following spring.

Leaves:

*Size.*—In a typical 4 year old specimen, larger than normal leaves which are approximately 3–4 inches wide by 4–5 inches long and deep green which turn a dark red in the fall and early winter. In a typical 6 year old specimen, the leaves are 4 inches wide and up to 7.5 inches long. While the leaf size is unique, the leaf coloring of 'Am-erika Touch-O-Pink' does not differ significantly from other dogwood varieties. Color in leaves lasts much longer than native dogwood.

Bloom:

*Number of flowers.*—Generally 2 to 4 per stem.

*Buds.*—2 to 4 blooms per branch on long stems, usually large.

*Size.*—Approximately 4–6 inches in diameter on the average.

*Color.*—Pink on the outer margins of the inner and outer pairs of bracts fading to almost white toward the center of the bracts. The outside edge of the bracts are a medium pink, towards the center it turns to a paler pink to almost white and the inflorescence is extremely large — from 4 to 6 inches across. They bloom consistently every year, whereas all other pinks and reds I have observed over the years do not have this characteristic. This is especially true in the lower Piedmont and Coastal Plains.

Development:

*Vegetation.*—Hardy.

*Blooming.*—Abundant, with first bloom in March in Tatnall County, Ga. with full bloom occurring in April, as observed in Tatnall County, Ga.

*Fruit.*—Borne in clusters of 8–18 berries. Each berry is oblong-shaped, approximately 0.75 inches long and 0.25 inches wide. The immature fruit are borne in the summer and are dark green in color, maturing to a bright red color in October.

Resistant to frost: Very Good.

Resistance to disease: Excellent resistance to anthracnose and insect borers.

What is claimed is:

1. A new and distinct variety of Dogwood tree, *Cornus florida*, named 'Am-erika Touch-O-Pink', characterized by the following combination of characteristics:

(a) forms extremely large and distinctive blooms wherein the petals are pink along the outer edge fading to almost white in the center;

(b) larger than normal leaves; and (c) superior growth rate and a hardy resistance to disease; substantially as herein shown and described.

* * * * *